United States Patent [19]

van der Weerdt et al.

[11] Patent Number: 4,459,224

[45] Date of Patent: Jul. 10, 1984

[54] PERFUME COMPOSITIONS AS WELL AS PERFUMED ARTICLES AND MATERIALS CONTAINING ALKYL SUBSTITUTED BENZYL CYANIDES AS A FRAGRANCE

[75] Inventors: Antonius J. A. van der Weerdt, Huizen; Roeland Plomp, Almere-Haven; Harmannus Boelens, Huizen, all of Netherlands

[73] Assignee: Naarden International N.V., Naarden-Bussum, Netherlands

[21] Appl. No.: 362,847

[22] Filed: Mar. 29, 1982

[30] Foreign Application Priority Data

Apr. 8, 1981 [NL] Netherlands .................. 8101739

[51] Int. Cl.$^3$ .............................................. A61K 7/46
[52] U.S. Cl. .......................... 252/522 R; 260/465 R; 252/174.11; 424/45
[58] Field of Search ................................. 252/522 R

[56] References Cited

U.S. PATENT DOCUMENTS 2,184,526 12/1939 Meuly ........................ 252/522 R
4,186,270 1/1980 Dowd et al. .................. 562/496

FOREIGN PATENT DOCUMENTS

EP62368 10/1982 European Pat. Off. .

OTHER PUBLICATIONS

Cosmetics and Perfumery, 1973, 88, pp. 46–48.
J. Med. Chem., 1980, 23, 1102–1108.
Chem. Abstracts 90:121148w.
Chem. Abstracts 82:144817n.
Perfume & Flavor Chemicals, S. Arctander, Monographs 302, 506, 641, 1451, 2717 and 2734.
Synthesis of Alkyl-Substituted 3-Phenyl-4-Hydroxycoumarins, B. Van Zantan et al., 79 Recueil (1960), 1211–1222.
Chem. Abstracts 63:13138e.

Primary Examiner—Anton H. Sutto
Attorney, Agent, or Firm—Brumbaugh, Graves, Donohue & Raymond

[57] ABSTRACT

Use of one or more alkyl substituted benzyl cyanides having the formula

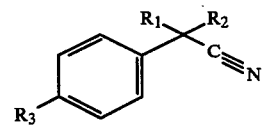

in which $R_1$ and $R_2$ each may represent a hydrogen atom or a methyl group and $R_3$ represents a branched alkyl group having at most 6 carbon atoms as a perfume component in perfume compositions and in imparting perfume notes to articles for example soaps, cleaning preparations and cosmetic compositions.

4 Claims, No Drawings

PERFUME COMPOSITIONS AS WELL AS PERFUMED ARTICLES AND MATERIALS CONTAINING ALKYL SUBSTITUTED BENZYL CYANIDES AS A FRAGRANCE

The invention relates to perfume compositions containing alkyl substituted benzyl cyanides as a fragrance as well as to products perfumed with these compounds.

For the past decade, there has been a continuous interest for the preparation and application of synthetic fragrances because these fragrances can always be prepared in the quantity desired and with uniform quality, this contrary to naturally occurring substances. Especially there is a demand for synthetic fragrances having a natural odor character and also a great chemical stability.

It was found that nitriles having the formula

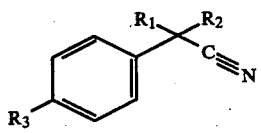

in which $R_1$ and $R_2$ each may present a hydrogen atom or a methyl group and $R_3$ represents a branched alkyl group having at most 6 carbon atoms, are strong and stable fragrances. The odor of the compounds according to the invention reminds one of algae and seaweed having ambergris like and fatty-animal notes. Further some compounds have muguet and cumin-like notes. Many of the compounds according to the invention are very suitable to impart a salty note which reminds one of the sea to perfume compositions. This applies especially to compounds wherein $R_3$ is an isopropyl- or tert.butyl group. This note was hardly obtainable with the fragrances known so far.

Benzyl cyanide is described as a fragrance having a spicy-green odor with sweet and strong floral notes (vide S. Arctander, Perfume and Flavor Chemicals, monograph no. 302). Therefore the odor of this compound differs completely from the odor of the compounds according to the invention. Up to now para-alkyl- and para-alkyl-alpha-alkyl substituted benzyl cyanides were unknown in the perfume industry. However, p-isopropyl- and p-tert.butyl-benzyl cyanide are described as intermediates in the synthesis of pharmaceuticals (vide Belgium patent specification No. 648,892, Chem. Abstr. 63 (1965), 13148f and B. van Zanten and W. Th. Nauta, Rec. Trav. Chim. 79 (1960), pages 1216–1217), but till now the olfactory properties of these compounds were not known.

In the last decade it appeared that the odor of many nitriles strongly resemble the odor of the corresponding aldehydes (vide S. Arctander, monograph no. 641 and no. 1451). The aldehydes corresponding to the nitriles according to the invention and as far as known in perfumery do have greenish odors which in no way resemble the above mentioned odors of the nitriles. For instance p-tert.butyl-phenyl acetaldehyde has a floral-green odor with woody notes (Arctander monograph 506). p-Iso-propyl phenyl acetaldehyde has a green and bark-woody odor (Arctander monograph 2734) and the corresponding α-methyl compound has a green, juicy or twiglike odor with a sharp spicy character (Arctander monograph no. 2718).

The compounds according to the invention may be prepared in a way known for analogous compounds for instance as described by B. van Zanten and W. Th. Nauta in Rec. Trav. Chim. 79 (1960), pages 1211–1223. As a starting compound the corresponding benzyl-bromide or -chloride can be used, which compound is converted into the nitrile with KCN or NaCN. With these reactions "phase-transfer-catalysis" can be used advantageously with a suitable catalyst like a tetra-alkyl-ammonium halide. The α-methyl- and α,α-dimethyl substituted compounds according to the invention may be prepared by methylating the corresponding p-alkyl-benzyl cyanides.

The compounds according to the invention may be used successfully in perfume compositions and in articles and materials to be perfumed for obtaining an algae- and weedlike, animal or muguet-like and especially a salty and "marine" note. Because of their great chemical stability these compounds are very suitable for perfuming of agressive materials like washing and cleaning agents as well as soap.

The phrase "perfume composition" means a mixture consisting of fragrances and optionally auxiliary substances which may be dissolved in an appropriate solvent or mixed with a powdery substrate and used to impart a desired odor to the skin and/or various products. Such perfume compositions as well as the compounds according to the invention per se may be used for perfuming of products. Examples of such perfumed products are: soaps, shower and bath products, washing agents, dish washing and cleaning agents, air fresheners and room sprays, pommanders, candles, cosmetics such as creams, ointments, lotions, colognes, pre- and after-shave lotions, talcum powders, hair care agents, body deodorants and antiperspirants.

Fragrances and mixtures thereof which in combination with the alkyl-substituted benzyl cyanides according to the invention can be used for the preparation of perfume compositions are e.g. naturally occurring products such as essential oils, absolutes, resinoids, resins, concretes etc., especially synthetic fragrances, such as hydrocarbons, alcohols, aldehydes, ketones, ethers, acids, esters, acetals, ketals, nitrile etc., covering saturated and unsaturated compounds, aliphatic, carbocyclic and heterocyclic compounds.

Examples of fragrances which may be used in combination with the compounds according to the invention are: geraniol, geranyl acetate, linalool, linalyl acetate, tetrahydrolinalool, citronellol, citronellyl acetate, dihydro myrcenol, dihydro myrcenyl acetate, tetrahydro myrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloromethylphenylcarbinyl acetate, p-tert. butylcyclohexyl acetate, isononyl acetate, vetiveryl acetate, vetiverol, α-hexylcinnamaldehyde aldehyde, 2-methyl-3-(p-tert.butylphenyl)-propanal, 2-methyl-3-(p-isopropyl phenyl)-propanal, 3-(p-tert.butylphenyl) propanol, tricyclodecenyl)acetate, tricyclodecenyl propionate, 4-(4-hydroxy-4-methylpentyl)-3-cyclohexene carbaldehyde, 4-(4-methyl-3-pentenyl)-3-cyclohexene carbaldedehyde, 4-acetoxy-3-pentyl-tetrahydropyran, 3-carboxymethyl-2-pentylcyclopentane, 2-n-heptylcyclopentanone, 3-methyl 2-pentyl-2-cyclopentanone, n-decanal, n-dodecanal, dec-9-en-1-ol, phenoxy-ethyl isobutyrate, phenylacetaldehyde dimethylacetal, phenylacetaldehyde diethylacetal, geranyl nitrile, citronellyl nitrile, cedryl acetate, 3-isocamphyl cyclohexanol, cedrylmethyl ether, isolongifolanon, aubepine nitrile, aubepine, heliotropine, coumarin, eugenol, vanillin, diphenyl oxide, hydroxy citronellal, ionones, methyl ionones, isomethyl ionones, irones, cis-3-hexenol and esters thereof, indan musk fragrances, tetralin musk fragrances, isochroman musk fragrances, macrocyclic ketones, macrolactone musk fragrances, ethylene brassylate, aromatic nitromuskl fragrances.

Auxiliary agents and solvents which may be incorporated into perfume compositions containing compounds according to the invention are e.g. ethanol, isopropanol, diethyleneglycol monoethylether, diethylphthalate etc.

The amount of the benzylcyanides according to the invention that can be used in a perfume composition or in a perfumed product can be varied within broad limits and depends e.g. on the product wherein the fragrance is used, the nature and the amount of the further components of the perfume composition and the odor effect desired. Therefore, it is only possible to indicate very broad limits, which give, however, a person skilled in the art sufficient information for an independant use of the compounds according to the invention. In most cases a quantity of only 0,001% by weight in a perfume composition is sufficient to obtain a clearly observable odor effect. On the other hand for obtaining special odor effects it is possible to use a quantity of 20% or more in a composition.

In products perfumed with the aid of perfume compositions according to the invention the concentration is proportionally lower and depends on the quantity of the composition used in the product.

The following examples only illustrate the preparation and the use of the compounds according to the invention and do not restrict the invention thereto.

EXAMPLE I p-Tert.butyl-benzyl cyanide

A mixture consisting of 107 g p-tert.butylbenzyl bromide, 2 g tetra butyl-ammonium jodide and 37 g NaCN in 50 ml water was heated during 1 hour at 100° C. After cooling the reaction mixture, the organic layer was separated and distilled in vacuo with a yield of 78 g of the desired cyanide. Then this product was fractionated in vacuo. Yield of p-tert.butylbenzyl cyanide: 65 g (80%): boiling point: 118° C./0,7 kPa: $n_D = 1,5110$. This cyanide has a very strong odor which reminds one of algae, seaweed and ozone with ambergris-like, fatty and animal notes.

EXAMPLE II p-Isopropyl-benzyl cyanide p-Isopropyl-benzyl chloride was obtained by vigorously stirring 100 g of the corresponding alcohol during 1 hour with a 2-fold excess of concentrated hydrochloric acid. Then the organic layer was distilled in vacuo with a yield of 101 g p-isopropyl-benzyl chloride.

A mixture consisting of 101 g p-isopropyl-benzyl chloride, 2 g tetrabutyl ammonium iodide and 50 g KCN in 50 ml water was heated to 100° C. during 1 hour. After cooling the layers were separated and the organic layer was distilled and thereafter fractionated in vacuo.

Yield of p-isopropyl-benzyl cyanide: 70 g (74%): boiling point: 124° C./0.7 kPa: $n_D^{25} = 1.5112$. The odor of isopropylbenzyl cyanide resembles strongly the odor of the above described tert.butyl-benzyl cyanide.

EXAMPLE III

α-Methyl- and α,α-dimethyl-p-tert.butyl-benzyl cyanide 36 g NaH and 173 g (1 mole) p-tert.butyl-benzyl cyanide, obtained according to example I were dissolved in a mixture consisting of 200 ml ether and 200 ml hexamethylphosphortriamide. To this mixture 213 g CH₃J was added in 90 minutes at a temperature of 20° C. The mixture was stirred during 3 hours and then washed with brine and evaporated. The residu was distilled in vacuo with a yield of 160 g distillate consisting of 70% α-methyl compound, 23% α,α-dimethyl compound and 7% starting product. The mixture was separated with GLC (gas liquid chromatography) (2 m column OV 17, temperature: 190° C.). α-Methyl-p-tert.butylbenzyl cyanide ($n_D^{24} = 1.5042$) has a very strong fresh odor with sea-, muguet- and cuminlike notes and a vague citruslike note. α,α-Dimethyl-p-tert.butylbenzyl cyanide ($n_D^{24} = 1.5018$) has a clear seaweed odor with fatty, cumin- and muguet notes.

EXAMPLE IV

A perfume composition for soap was prepared according to the following recipe:
100 parts by weight phenoxyethyl isobutyrate.
100 parts by weight phenylethyl alcohol.
100 parts by weight geraniol.
80 parts by weight 4-tert.butyl-cyclohexyl acetate.
70 parts by weight lavandin oil.
70 parts by weight 4-(4-hydroxy-4-methyl-pentyl)-cyclohexene-3-carbaldehyde.
50 parts by weight geranyl acetate.
50 parts by weight phenylethyl acetate.
50 parts by weight α-hexylcinnamaldehyde.
50 parts by weight α-n.pentylcinnamaldehyde.
50 parts by weight hexyl benzoate.
30 parts by weight musk ambrette.
30 parts by weight tricyclodecenyl propionate.
30 parts by weight tricyclodecenyl acetate.
20 parts by weight musk ketone.
20 parts by weight hexyl acetate.
10 parts by weight methylnonylacetaldehyde.
5 parts by weight undec-10-enal.
5 parts by weight p-isopropyl-benzyl cyanide, 10% solution in diethyl phthalate.

---

920 parts by weight.

A perfumed toilet soap was prepared by mixing thoroughly 1 kg of white soap grains, 20 g of above mentioned perfume composition and 10 g of a soap dye in a soap mill. Perfume coloured flakes were obtained, which were pressed in the usual way to toilet soap bars. The obtained toilet soap bars had a pleasant and stable odor.

EXAMPLE V

A perfume composition for air fresheners was prepared according to the following recipe:
150 parts by weight methylionon.
150 parts by weight bergamot oil.
50 parts by weight vetiveryl acetate
50 parts by weight hydroxycitronellal.
50 parts by weight Jasmin NB 114*
50 parts by weight ylang oil.
50 parts by weight geranium oil.
50 parts by weight Rosana NB 131*

50 parts by weight benzyl acetate.
30 parts by weight musk ketone.
30 parts by weight coumarin.
30 parts by weight sandalwood oil East-Indian.
25 parts by weight benzoë-resinoid Siam.
25 parts by weight Dianthal*
25 parts by weight rodinol.
25 parts by weight palma rosa oil.
25 parts by weight lemon oil Italian.
10 parts by weight 11-oxahexadekanolide.
10 parts by weight heliotropine.
10 parts by weight mousse de chene absolue.
5 parts by weight styrax-resinoid.
5 parts by weight undec-10-enol.
5 parts by weight methyl nonyl acetaldehyde
15 parts by weight p-tert.butylbenzyl cyanid, 10% solution in diethylphthalate.
--------------------
925 parts by weight.
*Perfume base marketed by Naarden International N.V.

With above perfume composition a room spray was prepared by mixing, 1.2 g of the perfume with 27.2 g of anhydrous ethanol, 2 g propylene glycol, 4.8 g diethylene glycol and 166 g freon. Aerosol-spray cans were filled with this mixture.

We claim:
1. Perfume composition containing one or more compounds having the formula

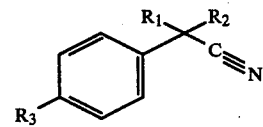

in which $R_1$ and $R_2$ each may represent a hydrogen atom or methyl group and $R_3$ represents a branched alkyl group having at most 6 carbon atoms.

2. Perfume composition according to claim 1 characterized by a content of at least 0.001% by weight of one or more of the compounds having the formula

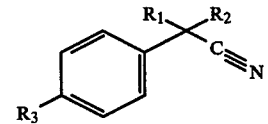

in which $R_1$, $R_2$ and $R_3$ do have the meanings mentioned in claim 1.

3. Perfumed products containing the perfume compositions as described in claim 1 or 2.

4. A perfume composition according to claim 1 wherein $R_3$ is selected from the group consisting of isopropyl and tertiary butyl groups.

* * * * *